United States Patent [19]

Manzer

[11] Patent Number: 5,345,016

[45] Date of Patent: * Sep. 6, 1994

[54] MANUFACTURE OF 1,1,1,2-TETRAFLUOROETHANE

[75] Inventor: Leo E. Manzer, Wilmington, Del.

[73] Assignee: E. I. Du Pont de Nemours and Company, Wilmington, Del.

[*] Notice: The portion of the term of this patent subsequent to Feb. 9, 2010 has been disclaimed.

[21] Appl. No.: 12,847

[22] Filed: Feb. 4, 1993

Related U.S. Application Data

[63] Continuation of Ser. No. 824,712, Jan. 17, 1992, Pat. No. 5,185,482, which is a continuation of Ser. No. 563,667, Aug. 3, 1990, abandoned, which is a continuation of Ser. No. 305,697, Feb. 3, 1989, abandoned.

[51] Int. Cl.$^5$ .................. C07C 17/08; C07C 17.20; C07C 19/02
[52] U.S. Cl. .................. 570/168; 570/156; 570/160; 570/165; 570/166
[58] Field of Search .................. 570/168, 165, 166

[56] References Cited

U.S. PATENT DOCUMENTS

| | | | |
|---|---|---|---|
| 2,458,551 | 1/1949 | Benning et al. | 570/168 |
| 2,637,747 | 5/1953 | McBee | 260/653 |
| 2,744,147 | 5/1956 | Milks | 260/653 |
| 2,744,148 | 5/1956 | Ruh et al. | 260/653.7 |
| 2,885,427 | 5/1959 | Ruh et al. | 260/653.7 |
| 2,946,827 | 7/1960 | Belf | 570/168 |
| 3,003,003 | 10/1961 | McGinty | 260/653.6 |
| 3,752,850 | 8/1973 | Scherer et al. | 260/544 F |
| 4,129,603 | 12/1978 | Bell | 260/653 |
| 4,158,675 | 6/1979 | Potter | 260/653.7 |
| 4,258,225 | 3/1981 | Feiring | 570/168 |
| 4,311,863 | 1/1982 | Gumprecht | 570/170 |
| 4,792,643 | 12/1988 | Sobolev | 570/168 |
| 4,922,037 | 5/1990 | Manzer | 57/168 |
| 5,051,537 | 9/1991 | Manzer | 570/168 |
| 5,185,482 | 2/1993 | Manzer | 570/168 |
| 5,243,105 | 9/1993 | Scott et al. | |
| 5,243,107 | 9/1993 | Scott et al. | |

FOREIGN PATENT DOCUMENTS

| | | |
|---|---|---|
| 0408005 | 7/1989 | European Pat. Off. . |
| 0328127 | 8/1989 | European Pat. Off. . |
| 0331991 | 9/1989 | European Pat. Off. . |
| 0446869 | 3/1990 | European Pat. Off. . |
| 0449614 | 3/1990 | European Pat. Off. . |
| 0502605 | 3/1991 | European Pat. Off. . |
| 0449617 | 10/1991 | European Pat. Off. . |
| 55-27138 | 2/1980 | Japan . |
| 640486 | 7/1950 | United Kingdom . |
| 1000485 | 8/1965 | United Kingdom . |
| 2030981 | 3/1983 | United Kingdom . |

*Primary Examiner*—Alan Siegel

[57] ABSTRACT

This invention provides an improved process for the manufacture of 1,1,1,2-tetrafluoroethane by the reaction of HF and trichloroethylene in the presence of a catalyst to form a mixture comprising 2-chloro-1,1,1-trifluoroethane and 1,1,1,2-tetrafluoroethane and, optionally, other organic by-products. The improvement resides in conducting the reaction in a single reaction zone while recovering the 1,1,1,2-tetrafluoroethane from the mixture and recycling the 2-chloro-1,1,1-trifluoroethane and, optionally, other organic by-products from the mixture to the reaction along with trichloroethylene and HF.

20 Claims, No Drawings

MANUFACTURE OF 1,1,1,2-TETRAFLUOROETHANE

This application is a continuation of application Ser. No. 824,712, filed Jan. 17, 1992 and issued as U.S. Pat. No. 5,185,482, which is a continuation of application Ser. No. 563,667 filed Aug. 3, 1990, now abandoned, which is a continuation of application Ser. No. 305,697, filed Feb. 3, 1989, now abandoned.

FIELD OF THE INVENTION

This invention relates to an improved catalytic process for the preparation of 1,1,1,2-tetrafluoroethane (HFC-134a) by the reaction of trichloroethylene with HF, whereby the reaction is conducted in a single reaction zone while recycling 2-chloro-1,1,1-trifluoroethane (HCFC-133a) with trichloroethylene to the reaction zone.

BACKGROUND OF THE INVENTION

U.S. Pat. No. 2,637,747 discloses the reaction of trichloroethylene and HF over an antimony pentachloride catalyst to obtain a 32% yield of HCFC-133a, no HFC-134a, and some 1,2-dichloro-1,1-difluoroethylene.

U.S. Pat. No. 2,744,147 discloses an alumina catalyst, which may be promoted with a metal (cobalt, nickel, and chromium), and a process using the catalyst in a fluidized bed for fluorinating haloalkanes at a temperature between 180° to 425° C. $CF_3CH_2Cl$ (HCFC-133a) is positively excluded from the list of halocarbons taught to be fluorinated by the invention process (Col. 1, lines 43–53, 54–65).

U.S. Pat. No. 2,744,148 discloses an alumina catalyst which may be promoted with a metal (chromium, cobalt, nickel, copper, and palladium) and a process for fluorinating haloalkanes to highly fluorinated products. A process is disclosed which activates the catalyst and converts at least part of the alumina to basic aluminum fluorides. $CF_3CH_2Cl$ (HCFC-133a) is again positively excluded from the list of halocarbons taught to be fluorinated by the invention process (Col. 2, lines 23–33, 34–46). U.S. Pat. No. 2,885,427 claims a process for forming a 1,1,1-trifluoro-2-haloethane by the reaction of HF and trichloroethylene over a basic chromium fluoride catalyst. Example 1 shows that this reaction affords the following products with the selectivities shown; HCFC-133a (94.2%), HFC-134a (3.6%), 1,2-dichloro-1-fluoroethylene (2.0%), and pentafluoroethane (0.2%); the conversion of trichloroethylene is 92.3%.

U.S. Pat. No. 3,003,003 claims a process for the manufacture of HCFC-133a by reacting trichloroethylene and HF over an antimony fluorochloride catalyst. In Example 2 a 67% yield of HCFC-133a is reported for this reaction.

GB 1,000,485 claims a process for the preparation of fluorinated organic compounds by passing a halo-olefin and HF over a catalyst consisting essentially of activated alumina which is partially fluorinated. The alumina catalyst may also contain polyvalent metals chosen from chromium, cobalt, nickel, and manganese. The patent discloses that the use of $AlF_3$ as a catalyst is not always satisfactory partly because it "leads to several reaction by-products which may be present in large quantities" (page 2, lines 20–24). In Example 1, trichloroethylene is reacted with HF over a fluorinated alumina containing chromium and cobalt to yield HCFC-133a with a 94.1% selectivity, fluorinated olefins with a 2.7% selectivity and no HFC-134a.

U.S. Pat. No. 3,752,850 discloses a process for the manufacture of HCFC-133a by reacting trichloroethylene and HF in the presence of a catalyst, the composition of which can vary between $CrF_{1.5}O_{1.5}$ and $CrF_2O$, or a catalyst, the composition of which can vary between $CrFO_2$ and $CrF_2O$. In Example 8 it is shown that the process of the invention affords HCFC-133a in 94.8% yield and no HCFC-134a.

U.S. Pat. No. 4,129,603 discloses a process for the manufacture of HFC-134a which comprises reacting in the vapor phase at elevated temperature a haloethane of formula $CX_3CH_2Y$, wherein X is Br, Cl, or F and Y is Cl, with HF in the presence of a catalyst which is chromium oxide or which is at least in part basic chromium fluoride and wherein the HFC-134a product containing 1-chloro-2,2-difluoroethylene, which is an impurity, is removed by intimate contact with a metal permanganate in a liquid medium.

U.S. Pat. No. 4,158,675 discloses a process for the manufacture of HFC-134a which comprises reacting in the vapor phase at elevated temperature (300° to 400° C.) a haloethane of formula $CX_3CH_2Y$, wherein X is Br, Cl, or F and Y is Cl, with HF in the presence of a catalyst which is chromium oxide or which is at least in part basic chromium fluoride and wherein the HFC-134a product stream containing 1-chloro-2,2-difluoroethylene, which is an impurity, and HF is brought into contact over said catalyst at a temperature in the range of 100° to 275° C.

U.S. Pat. No. 4,258,225 discloses the reaction of trichloroethylene and HF over a $TaF_5$ catalyst to yield a mixture containing 1,2-dichloro-1,1-difluoroethane (41%), 1,1,2-trichloro-1-fluoroethane (57%), and 1,1,1,2-tetrachloroethane (2%).

GB 2,030,981 claims a process for the preparation of HFC-134a which comprises reacting HCFC-133a with HF in molar excess at a temperature not lower than 300° C. in the presence of an inorganic chromium (III) compound with the introduction of 0.002 to 0.05 mol $O_2$ per mol of HCFC-133a into the reaction system. The patent also states that in this process, if the oxygen content is below the lower limit, catalyst deterioration occurs. When the oxygen content is more than the upper limit, catalyst deterioration is not a problem but the selective conversion to HFC-134a decreases. It is believed that this decrease in selectivity occurs because the catalyst promotes the oxidation of hydrogen chloride to molecular chlorine and water. [See Chemical Week, page 18, Jun. 24, 1987 for the use of chromium based catalysts for the oxidation of hydrochloric acid to chlorine and water]. The highest yield of HFC-134a reported is 29%.

JP 55-27138 claims a process for the preparation of HFC-134a by the reaction of HCFC-133a and HF in the presence of an inorganic chromium (III) compound. The highest yield of HFC-134a reported is 35%.

U.S. Pat. No. 4,792,643 discloses a process for the manufacture of HFC-134a by the reaction of $CX_2=CHX$, in which X is chlorine or bromine or a combination of both, with HF in the vapor phase at about 300° C. to about 500° C. over a catalyst prepared by codepositing hexavalent chromium oxide and a compound of a transition metal selected from the group consisting of titanium, zirconium, vanadium, molybdenum, and manganese on alumina, which is then contacted with HF, to form a product mixture from which HFC-134a is recovered. In one example 68% of trichloroethylene is converted to products with the following selectivities: 20% HFC-134a, 50% HCFC-133a and 30% other products, which include CClF=CHCl (FC-1121), CCl$_2$=CHF (FC-1121a), CF$_3$CHClF (HCFC-124), CHF$_2$CClF$_2$ (HCFC-124a) and CF$_3$CH$_3$ (HFC-143a). It is disclosed that HCFC-133a is available for further reaction either by extending the catalyst contact time, raising the temperature, or recycling.

The catalyzed reaction of HF with trichloroethylene to afford HFC-134a is a sequential reaction. The intermediate, HCFC-133a, can be produced in essentially quantitative yield; however the conversion in the second reaction of HCFC-133a with HF to yield final product, HFC-134a, is dependent on the HF/HCFC-133a ratio, the higher the ratio, the more HFC-134a is produced at a given temperature. In general, HCFC-133a is isolated as an intermediate and fed to a second reactor where the conversion to HFC-134a is conducted. A need exists for the manufacture of HFC-134a from trichloroethylene and HF without simultaneously producing significant amounts of deleterious by-products or the requirement of two reactors, one for making HCFC-133a and one for making HFC-134a from HCFC-133a, which increases the cost of manufacture. This is particularly true in view of the growing demand for commercial quantities of HFC-134a as an environmentally desirable refrigerant. The herein described invention affords HFC-134a from the reaction of trichloroethylene and HF with very little (less than 5%) by-products in a single reaction zone.

SUMMARY OF THE INVENTION

This invention provides an improved process for the manufacture of 1,1,1,2-tetrafluoroethane (HFC-134a) by the reaction of HF and at least one of trichloroethylene and 2-chloro-1,1,1-trifluoroethane (HCFC-133a) in the presence of a catalyst at elevated temperature to form a mixture comprising 2-chloro-1,1,1-trifluoroethane (HCFC-133a) and 1,1,1,2-tetrafluoroethane (HFC-134a) and, optionally, other organic by-products. The improvement resides in conducting the reaction in a single reaction zone, preferably, in the presence of a catalyst composition comprising at least one metal selected from the group consisting of chromium, Group VIII, Group VIIB, Group IIIB, Group IB and metals having an atomic number from 58 to 71, said metal preferably on an aluminum fluoride or carbon support, while (1) recovering the 1,1,1,2-tetrafluoroethane (HFC-134a) from the mixture and (2) recycling the 2-chloro-1,1,1-trifluoroethane (HCFC-133a) and, optionally, other organic by-products from the mixture to the reaction along with trichloroethylene in a molar amount at least equal to the molar amount of 1,1,1,2-tetrafluoroethane (HFC-134a) recovered from the mixture plus the molar amount of other organic by-products, which may be formed, and with additional HF in a molar amount from 3 to 30 times the molar amount of trichloroethylene. The amount of trichloroethylene utilized in the recycle (2) in accordance with this invention is intended to include any unreacted trichloroethylene which may be present in the mixture when HF is initially reacted with trichloroethylene.

In the practice of this invention only minor amounts, i.e. less than 10% by weight and more commonly less than 5% by weight, of other organic byproducts, such as fluorinated ethylenes and other unsaturated haloolefins, are formed. Consequently, for all practical purposes the molar amount of trichloroethylene can be substantially at least equal to the molar amount of 1,1,1,2-tetrafluoroethane (HFC-134a) recovered. A key feature of the invention is that through control of recycle and, optionally, preferable catalyst selection, as described herein, the desired tetrafluoroethane can be obtained as the major product at greater than 99% trichloroethylene conversion with a reduction in the number of process steps for producing HFC-134a from trichloroethylene via HCFC-133a.

DETAILS OF THE INVENTION

The catalyst composition preferably utilized in the practice of this invention must contain at least one metal from the group described above, preferably on an aluminum fluoride or carbon support. By aluminum fluoride is meant at least one of AlF$_3$ and fluorided alumina. The AlF$_3$ and/or fluorided alumina can be prepared by any method known in the art or described hereinbelow. By fluorided alumina is meant a high fluorine content composition comprising aluminum, oxygen, and fluorine in such proportions that the total fluorine content of the catalyst composition taken as AlF$_3$ is, preferably, at least 50 weight percent, exclusive of any metal which is present, and more preferably 90 weight percent of the catalyst composition.

The total amount of metal, expressed as the metal, should be a catalytically effective amount and is generally less than 50% by weight of the catalyst composition and preferably less than 20% by weight of the catalyst composition, and usually at least 0.02% by weight of the catalyst composition. A more preferred range is 0.1 to 10% by weight of the catalyst composition. The remainder of the catalyst composition may include alumina or aluminum oxyfluoride.

The form of the catalyst is not critical and may be used in the form of pellets, powders or granules.

In the practice of this invention the reaction of trichloroethylene with HF can be conducted in the presence or absence of oxygen. When conducted in the presence of oxygen the preferred metal of the catalyst composition is selected from at least one of cobalt, chromium, manganese, nickel, palladium, silver and ruthenium. In addition, when oxygen is present the catalyst composition, when supported, should be supported on an aluminum fluoride, rather than on carbon.

The catalyst can be prepared in any manner known to the art. For example, the catalyst can be prepared by impregnating alumina or aluminum oxyfluoride with a solution of at least one metal selected from the group consisting of chromium, Group VIII (iron, cobalt, nickel, ruthenium, rhodium, palladium, osmium, iridium, platinum), Group VIIB (manganese, technetium, rhenium), Group IIIB (scandium, yttrium, lanthanum), Group IB (copper, silver, gold) and metals having an atomic number from 58 to 71 (cerium, prasedymium, neodymium, promethium, samarium, europium, gadolonium, terbium, dysprosium, holmium, erbium, thulium, ytterbium, lutetium), which may be in the form of any soluble compound of the metal such as the oxide, oxyhalide, halide, pseudohalide, nitrate, sulfate, or organic salt such as acetate, propionate and any other compound of said metals which is convertible to a metal fluoride under the reaction conditions described herein. The halides include chlorides, fluorides, and bromides. The pseudohalides includes cyanides, cyanates and thiocyanates. The preferred metals are chromium and cobalt in combination. It is further preferred that the chromium utilized in the practice of this invention be trivalent chromium.

In addition, when it is desired that the metal be supported on an aluminum fluoride, the catalyst can also be prepared by co-precipitation of the catalytic metal and the aluminum as the hydroxides which are thereafter dried and calcined to form the mixed oxides, a technique well known to the art. The resulting oxide can be fluorinated as described herein.

Generally, the catalyst composition preferred for use in the present invention will be pretreated with HF or other vaporizable compounds containing fluorine such as $SiF_4$, $CCl_3F$, $CCl_2F_2$, $CHF_3$ or $CCl_2FCClF_2$ to activate the catalyst. This pretreatment is accomplished by placing the catalyst composition in a suitable container which can be the reactor to be used to perform the reaction of the instant invention, and thereafter, passing HF over the dried catalyst composition. This is conveniently carried out by passing HF over the catalyst for a period of time, for example, of about 15 to 300 minutes at a temperature of, for example, about 200° C. to 450° C. Nevertheless, this pretreatment is not essential; initial process conditions and equipment could be selected so as to activate the catalyst under initial process conditions.

By vaporizable fluorine-containing compound is meant a fluorine-containing compound which will convert the catalyst of the instant invention to the desired degree of fluorination using the pretreatment conditions described herein.

The reaction of trichloroethylene with HF in the presence of the catalyst of the instant invention is conducted at about 300° to 500° C., preferably about 350° to 425° C., and most preferably about 370° to about 410° C., with a contact time of about 0.1 to about 60 seconds, preferably about 5 to about 30 seconds.

The amount of HF should be at least a stoichiometric amount. Generally, the molar ratio of additional HF to trichloroethylene recycled with HCFC-133a can range from about 3/1 to about 30/1, preferably about 5/1 to 15/1, and more preferably about 5/1 to 10/1.

The amount of oxygen which may be present during the reaction relative to a mole of trichloroethylene and HCFC-133a can vary but will generally range from 0.001 to 1.0 moles. The oxygen may be fed to the reaction zone as such or may be diluted with an inert gas such as nitrogen, helium, or argon. The source of the oxygen may also be air containing molecular oxygen.

The catalyst preferred for use when oxygen is present in accordance with this invention also has the ability to minimize the oxidation of hydrogen chloride to molecular chlorine and water. The main disadvantage of this side reaction is that chlorine in the presence of HF reacts with $CF_3CH_2F$ to produce $CF_3CHFCl$ (HCFC-124) or it can react with $CF_3CH_2Cl$ to produce $CF_3CHCl_2$ (HCFC-123). Both HCFC-123 and HCFC-124 can then further react with HF to produce $CF_3CF_2H$. This reaction with $Cl_2$ results in a significant yield loss of the desired product $CF_3CH_2F$. In addition the formed water in combination with HF is very corrosive.

In general, with a given catalyst composition, the higher the temperature, the greater the HF/trichloroethylene mol ratio, and the longer the contact time, the greater is the conversion to fluorinated products and the greater is the production of polyfluorinated products. Utilizing this invention, the above variables can be balanced, one against the other, so that formation of $CF_3CH_2F$ is maximized and formation of the more highly fluorinated $CF_3CHF_2$ is minimized.

The reaction of trichloroethylene with HF may be conducted in any suitable reactor, including fixed and fluidized bed reactors. The reaction vessel should be constructed from materials which are resistant to the corrosive effects of hydrogen fluoride such as Inconel ® alloy and Hastelloy ® alloy.

Pressure is not critical. Atmospheric and superatmospheric pressures are the most convenient and are therefore preferred.

EXAMPLES

In the following illustrative examples, all parts are by weight, all percentages are molar, and all temperatures are Celsius unless otherwise stated. All reactions used commercial HF containing only trace amounts of water.

General Procedure for Fluorination

The reactor (a 0.5 inch ID, 12 inch long Inconel ® alloy pipe) was charged with the amount of catalyst as described in the following examples, and placed in a sand bath. The bath was gradually heated to 400° C. while $N_2$ gas at a flow rate of 50 cc/min was passed through the reactor to remove traces of water. The temperature was lowered to 200° C. and HF and $N_2$ gas (¼ molar ratio) were passed through the reactor and the $N_2$ flow was decreased with time until neat HF was being passed through the reactor. At this point the temperature was gradually raised to 425° C. and maintained there for 15 to 300 minutes.

The temperature was then decreased to the indicated value and, thereafter, the other reactant flows were started. The flows were adjusted to give the indicated molar ratios and contact times in the Examples.

The reactor effluent was sampled on-line with a Hewlett Packard HP 5890 gas chromatograph using a 20 foot long, one-eighth inch diameter, column containing Krytox ® perfluorinated polyether on an inert support and a helium flow of 35 cc/min. Gas chromatographic conditions were 70° C. for three minutes followed by temperature programming to 180° C. at a rate of 6° C./minute.

EXAMPLE 1

Fluorination of Trichloroethylene with HCFC-133a Recycle

The general procedure for fluorination was followed using 19.0 g (30 mL) of $CoCl_2/Al_2O_3$ (2% Co) as the initial catalyst charge. The HF/133a/trichloroethylene/$O_2$ molar ratio was 10/1/0.2/0.2. The product stream resulting from the reaction of HF with HCFC-133a, trichloroethylene and air over the prepared catalyst with a 20 second contact time at 390° C. and after a reaction run of 53 hours showed the following: 17.4% $CF_3CH_2F$ (HFC-134a), 80.8% $CF_3CH_2Cl$ (HCFC-133a), 1.2% $CF_2=CHCl$ (FC-1122), 0.3% $C_2HCl_2F$ (FC-1121, two isomers), 0.1% trichloroethylene and 0.2% $CH_2F_2$.

The conversion of trichloroethylene was greater than 99% and the ultimate selectivity to HFC-134a with recycle of the HCFC-133a, FC-1122 and FC-1121 is greater than 98%.

EXAMPLES 2-7

Fluorination of Trichloroethylene with HCFC-133a Recycle

The general procedure for fluorination was followed using 21.1 g (30 mL) of (CoCl$_2$+CrCl$_3$)/Al$_2$O$_3$ (1% Co+1% Cr) as the initial catalyst charge. The results of the reaction of HF with either HCFC-133a and trichloroethylene, or HCFC-133a, trichloroethylene, and air over the prepared catalyst with a 20 second contact time are give in Table 1. The HF/133a/trichloroethylene/O$_2$ molar ratio was 10/1/0.2/0 for Examples 2–4 and 10/1/0.2/0.2 for Examples 5–7.

TABLE 1

| Ex. | Hrs | Temp | % CF$_3$CH$_2$F | % CF$_3$CH$_2$Cl | % CF$_3$CF$_2$H | % CFCl=CHCl |
|---|---|---|---|---|---|---|
| 2 | 2 | 380° C. | 29.3 | 65.6 | 0.8 | 0.1 |
| 3 | 5 | 360 | 28.5 | 68.9 | 0.3 | 0.0 |
| 4 | 17 | 350 | 26.2 | 72.3 | 0.0 | 0.0 |
| 5 | 50 | 350 | 15.3 | 83.5 | 0.0 | 0.0 |
| 6 | 94 | 370 | 18.5 | 79.5 | 0.1 | 0.1 |
| 7 | 120 | 400 | 18.4 | 74.7 | 1.0 | 0.2 |

EXAMPLES 8-14

Fluorination of Trichloroethylene with HCFC-133a Recycle

The Inconel ® reactor was charged with 31.0 g (30 mL) Cr$_2$O$_3$. The results of the reaction of HF with either HCFC-133a and oxygen, or HCFC-133a, trichloroethylene, and oxygen over the catalyst with a second contact time are given in Table 2. The HF/133a/trichloroethylene/oxygen molar ratio was 10/1/0/0.2 for comparative examples 8 and 9 and 10/1/0.2/0.2 for 10–14. Comparison of these results with Examples 1–7 clearly show that the preferred catalyst embodiment of this invention provides many advantages, one of which is the fact that the chlorination chemistry which occurs with the catalyst of examples 8–14 affords significant amounts of by-products. Significant amounts of by-products are not formed when using the catalysts shown in Examples 1–7.

TABLE 2

| Ex. | Hrs | Temp | % CF$_3$CH$_2$F | % CF$_3$CH$_2$Cl | % CF$_3$CFHCl | % CF$_3$CF$_2$H | % CF$_3$CH$_3$ | % CHF$_3$ |
|---|---|---|---|---|---|---|---|---|
| 8 | 3 | 330° C. | 24.0 | 68.7 | 2.6 | 1.9 | 0.0 | 1.0 |
| 9 | 5 | 350 | 23.2 | 62.5 | 3.3 | 7.2 | 0.0 | 1.7 |
| 10 | 17 | 350 | 15.7 | 72.6 | 3.5 | 5.0 | 0.0 | 0.9 |
| 11 | 23 | 370 | 12.2 | 72.6 | 1.5 | 10.9 | 0.3 | 0.9 |
| 12 | 26 | 390 | 12.5 | 68.3 | 0.6 | 13.8 | 1.5 | 1.5 |
| 13 | 29 | 410 | 10.8 | 57.2 | 1.2 | 22.2 | 3.1 | 2.5 |
| 14 | 31 | 430 | 7.4 | 39.5 | 2.4 | 36.9 | 5.0 | 4.2 |

What is claimed:

1. A process for the manufacture of 1,1,1,2-tetrafluoroethane wherein HF is reacted with trichloroethylene in a reaction zone in the presence of a catalyst composition at elevated temperature to form a product mixture comprising 1,1,1,2-tetrafluoroethylene, 2-chloro-1,1,1-trifluoroethane and optionally, other organic by-products, and wherein 1,1,1,2-tetrafluoroethane is recovered from the product mixture, characterized by:

passing HF over the catalyst composition at a temperature from about 200° C. to 450° C.;
   recycling a portion of the product mixture including the 2-chloro-1,1,1,-trifluoroethane therein to the reaction zone;
   adding to reaction zone additional trichloroethylene in a molar amount at least equal to the molar amount of 1,1,1,2-tetrafluoroethane recovered from the mixture and additional HF in a molar amount from 3 to 30 times the molar amount of additional trichloroethylene;
   conducting the reaction of the trichloroethylene with HF and the reaction of 2-chloro-1,1,1-trifluoroethane with HF at a temperature and at a contact time and in the presence of a catalyst composition selected to form a product mixture comprising 1,1,1,2-tetrafluoroethane and 2-chloro-1,1,1-trifluoroethane, and having less than about 10 percent by weight of said other organic by-products; and
   recovering 1,1,1,2-tetrafluoroethane from the product mixture as the major product of the process;
   said catalyst composition comprising at least one metal selected from the group consisting of trivalent chromium, Group VIII, Group IIIB, Group IB and metals having an atomic number from 58 to 71.

2. A process in accordance with claim 1 wherein the catalyst composition is activated by passing HF over the catalyst composition under initial process conditions; and wherein the catalyst composition contains said at least one metal on an aluminum fluoride support.

3. A process in accordance with claim 1 wherein the catalyst composition comprises trivalent chromium.

4. A process in accordance with claim 3 wherein the catalyst composition comprises trivalent chromium on an aluminum fluoride support.

5. A process in accordance with claim 3 wherein the reaction zone includes a fluidized bed reactor.

6. A process in accordance with claim 1 wherein the catalyst composition comprises trivalent chromium and a divalent metal.

7. A process in accordance with claim 1 wherein the catalyst composition comprises trivalent chromium and divalent cobalt.

8. A process in accordance with claim 1 wherein the reaction zone includes a reactor selected from fixed and fluidized bed reactors.

9. A process for producing 1,1,1,2-tetrafluoroethane wherein HF is reacted with 2-chloro-1,1,1-trifluoroethane in a reaction zone in the presence of a catalyst composition at elevated temperature to form a product mixture comprising 1,1,1,2-tetrafluoroethane, 2-chloro-1,1,1-trifluoroethane, and optionally other organic byproducts, and wherein 1,1,1,2-tetrafluoroethane is recovered from the product mixture, characterized by:

passing HF over the catalyst composition at a temperature from about 200° C. to 450° C.;

recycling a portion of the product mixture including the 2-chloro-1,1,1-trifluoroethane therein to the reaction zone;

adding to the reaction zone trichloroethylene in a molar amount at least equal to the molar amount of 1,1,1,2-tetrafluoroethane recovered and additional HF in a molar amount 3 to 30 times the molar amount of trichloroethylene added;

conducted the reaction of said 2-chloro-1,1,1-trifluoroethane with HF and the reaction zone at a temperature and at a contact time and in the presence of a catalyst composition selected to form a product mixture having less than 10 percent by weight of said other organic by-products; and recovering 1,1,1,2-tetrafluoroethane from the product mixture as the major product of the process;

said catalyst composition comprising at least one metal selected from the group consisting of trivalent chromium, Group VIII, Group IIIB, Group IB and metals having an atomic number from 58 to 71.

10. A process in accordance with claim 9 wherein the catalyst composition is activated by passing HF over the catalyst composition under initial process conditions; and wherein the catalyst composition includes said at least one metal on an aluminum fluoride support.

11. A process in accordance with claim 9 wherein the catalyst composition comprises trivalent chromium.

12. A process in accordance with claim 11 wherein the catalyst composition comprises trivalent chromium on an aluminum fluoride support.

13. A process in accordance with claim 9 wherein the reaction zone includes a fluidized bed reactor.

14. A process in accordance with claim 9 wherein the catalyst composition comprises trivalent chromium and a divalent metal.

15. A process for the manufacture of 1,1,1,2-tetrafluoroethane wherein HF is reacted with both trichloroethylene and 2-chloro-1,1,1-trifluoroethane in the presence of a catalyst composition at elevated temperature to form a product mixture comprising 1,1,1,2-tetrafluoroethane, 2-chloro-1,1,1-trifluoroethane and other organic by-products, and wherein 1,1,1,2-tetrafluoroethane is recovered, characterized by:

passing HF over the catalyst composition at a temperature from about 200° C. to 450° C.;

using trichloroethylene in a molar amount at least equal to the 1,1,1,2-tetrafluoroethane recovered;

using at least a stoichiometric amount of HF;

producing a product mixture containing 1,1,1,2-tetrafluoroethane and 2-chloro-1,1,1-trifluoroethane together with other organic by-products from said reaction to trichloroethylene with HF and said reaction of 2-chloro-1,1,1-trifluoroethane with HF in the presence of said catalyst composition with isolating 2-chloro-1,1,1-trifluoroethane;

recovering 1,1,1,2-tetrafluoroethane from the product mixture as the major product of the process; and recycling a portion of the product mixture including the 2-chloro-1,1,1-trifluoroethane and other organic by-products of said product mixture to said reaction of 2-chloro-1,1,1-trifluoroethane in the presence of said catalyst composition, for further production of 1,1,1,2-tetrafluoroethane without isolating the 2-chloro-1,1,1-trifluoroethane of said recycled portion from other organic by-products of said recycled portion;

said catalyst composition by-products of said recycled portion; selected from the group consisting of trivalent chromium, Group VIII, Group IIIB, Group IB, and metals having an atomic number from 58 to 71.

16. A process in accordance with claim 15 wherein the catalyst composition is activated by passing HF over the catalyst composition under initial process conditions; and wherein the catalyst composition includes said at least one metal on an aluminum fluoride support.

17. A process in accordance with claim 15 wherein the catalyst composition comprises trivalent chromium.

18. A process in accordance with claim 15 wherein the catalyst composition comprises trivalent chromium on an aluminum fluoride support.

19. A process in accordance with claim 15 wherein the composition comprises trivalent chromium and a divalent metal.

20. A process in accordance with claim 15 wherein the other organic by-products of the product mixture comprise halogenated ethylenes containing fluorine; and wherein said recycle is conducted without isolating 2-chloro-1,1,1-trifluoroethane from halogenated ethylenes containing fluorine.

* * * * *

UNITED STATES PATENT AND TRADEMARK OFFICE
CERTIFICATE OF CORRECTION

PATENT NO. : 5,345,016
DATED : September 6, 1994
INVENTOR(S) : Leo E. Manzer

It is certified that error appears in the above-identified patent and that said Letters Patent is hereby corrected as shown below:

At column 5, line 31, please delete "HE" and insert in its place -- HF --.

In Claim 9 (column 9, line 13), please delete "conducted" and insert in its place -- conducting --.

In Claim 9 (column 9, line 14), please insert the words -- of said trichloroethylene with HF in said reaction -- after the word "reaction".

In Claim 15 (column 10, line 11), please delete "with" and insert in its place -- without --.

In Claim 15 (column 10, lines 25-26), please delete the phrase "by-products of said recycled portion;" (an erroneous repetition) and insert in its place the phrase -- comprising at least one metal --.

Signed and Sealed this

Twenty-fifth Day of August, 1998

Attest:

BRUCE LEHMAN

Attesting Officer

Commissioner of Patents and Trademarks